United States Patent [19]

Frick

[11] Patent Number: 4,542,823
[45] Date of Patent: Sep. 24, 1985

[54] MIXING CONTAINER

[75] Inventor: Hansjörg Frick, Schaan, Liechtenstein

[73] Assignee: Etablissement Dentaire Ivoclar, Schann, Liechtenstein

[21] Appl. No.: 663,289

[22] Filed: Oct. 22, 1984

Related U.S. Application Data

[63] Continuation of Ser. No. 513,600, Jul. 14, 1983, abandoned.

[30] Foreign Application Priority Data

Jul. 22, 1982 [DE] Fed. Rep. of Germany ....... 3227432

[51] Int. Cl.⁴ .............................................. B65D 25/08
[52] U.S. Cl. ..................................... 206/220; 366/602
[58] Field of Search ............... 366/130, 241, 602, 348, 366/349, 255; 206/219–222; 215/DIG. 8

[56] References Cited

U.S. PATENT DOCUMENTS 4,182,447 1/1980 Kay ..................................... 206/220

FOREIGN PATENT DOCUMENTS 519008 4/1953 Belgium .............................. 206/220

Primary Examiner—Timothy F. Simone
Attorney, Agent, or Firm—Sprung Horn Kramer & Woods

[57] ABSTRACT

Mixing container for manufacturing dental preparations with a first part that contains a powdered material and a second, separable part that contains a liquid in a destructible foil bag.

The bag is destroyed by a movable pestle. The resistance to ripping of the foil bag and the pressure impulse acquired by the pestle when the container is shaken in an oscillating mixer are proportioned to result in the destruction of the bag when struck by the pestle. The pestle has elevations and guides in preferred embodiments.

13 Claims, 2 Drawing Figures

MIXING CONTAINER

This is a continuation, of application Ser. No. 513,600, filed July 14, 1983, ABND.

BACKGROUND OF INVENTION

1. Field of Invention

The invention concerns a mixing container for separately storing and mixing interactive materials used in manufacturing dental preparations, especially amalgams.

2. Discussion of Prior Art

Known mixing containers of this type (see for example German Auslegeschrift No. 1 287 251) have a part in the form of a mixing compartment that contains a, normally powdered, material such as silver powder, and another, separable part separated by a wall from the mixing compartment and containing a liquid, mercury for instance. The separating wall is usually part of a destructible foil bag in which the liquid is sealed into and is disposed adjacent a perforated separation between the two parts. Displacing the parts in relation to each other destroys the foil bag, placing the two compartments in communication. The liquid is forced into the mixing compartment, where it is intimately mixed with the powdered material, preferably by clamping the mixing container in the fork of an automatic oscillating mixer called an amalgam mixer.

Although such mixing containers have generally proven themselves in practice, they still have certain drawbacks. The perforated separation that functions as a support and counterpressure surface is an additional component that increases the costs of manufacturing the container. Furthermore, it is necessary in order to get sufficient liquid out of the foil bag to make the pressure surface of the perforated separation and the inside of the front wall of the second part as similar in shape and size as possible. This necessitates relatively precise manufacturing tolerances, although this can, in practice, be compensated for by positioning a rubber disk between the cover and the foil bag. Furthermore, a separate instrument is necessary to open the bag and empty it adequately.

Mixing containers of this type are also known in which the mixing compartment has a movable oblong pestle. Such a container is described for example in German Offenlegungsschrift No. 2 931 262. The wall is a movable and flexible separating structure in the form of a disk or stuffing with its edge resting against and sealing off the inside of the wall of the first part. Since the liquid is not sealed into a foil, separate storage of the interactive materials can not be guaranteed. The pestle in the mixing compartment forces the separating structure against the upper wall and mixes the two materials after the liquid has been transferred into the mixing compartment.

Another mixing container of this type described in German Offenlegungsschrift No. 1 566 222 has two mutually displaceable parts separated by a foil, one containing a liquid (mercury and the other a powder (metal). The second part, which is shaped like a cap, contains, along with the powder, a pestle that rips or cuts the separating foil, which has weakening lines, when the two parts of the container are mutually displaced so that the powdered metal can combine with the mercury. The materials are then mixed in an oscillating mixer.

The disadvantages of such a mixing container are that the liquid cannot be sealed off absolutely gas-tight and that the separating foil can rip when the two parts are displaced relative to each other by accident. Scraps of separating foil can also get into the finished mixture.

The present invention is intended as a mixing container of the type described in the foregoing that has a simple design in which the liquid is safely preserved before use and quantitatively transferred into the mixing compartment, where the two materials are intimately fixed. Furthermore, no additional instrument is needed to extensively transfer the liquid.

The object of the invention is accordingly a mixing container for separately storing and mixing interactive materials used in manufacturing dental preparations, especially amalgams and having a mixing compartment that contains a, normally powdered, material such as silver powder, another, separable part separated by a wall from the mixing compartment and containing a liquid, mercury for instance, and a movable oblong pestle in the mixing compartment. The separating wall is the wall facing the mixing compartment of a liquid-filled destructible foil bag in the second part. The resistance to ripping of the foil bag and the pressure impulse acquired by the pestle when the container is shaken in a oscillating mixer are matched to result in the destruction of the bag when struck by the pestle.

The resistance to ripping of the destructible foil bag is determined by its thickness and material properties (elasticity, brittleness, etc.) and may also be affected for example by a pre-set ripping point in the wall of the bag facing the mixing compartment.

The term "pressure impulse" has been somewhat arbitrarily adapted from the physical concept of impulse. It is a function of the mass of the pestle, of the (negative) acceleration of the pestle as it strikes the foil bag, and of the time during which the pestle acts on the bag. The last two parameters are determined by the particular type of oscillating mixer employed. If the mixer moves rapidly and with a high amplitude, the force exerted by the pestle on the foil bag when it brakes upon contact will be more powerful than if the mixer moves slowly and with a low oscillation amplitude. The time during which the pestle acts on the bag essentially depends on the length of the mixing process and the oscillating frequency of the mixer. The dimension of the pressure impulse imparted by the pestle on the foil bag is also an inverse function of the surface of impact. Thus, the pressure impulse can be increased for example by an elevation, preferably a point, which can even be conical, on the surface of the pestle that faces the bag. The pressure impulse can be decreased on the other hand by increasing the area of contact between the pestle and the bag. In this case, either the mass of the pestle and/or the speed, amplitude, frequency or duration of oscillation must be increased to destroy a foil bag of constant foil thickness and material properties. These relationships are easy to confirm empirically. If it is discovered for example that a given foil bag is not destroyed by a pestle of a specific mass at a specific intensity and length of oscillation, the mass of the pestle can be increased or a point can be added to it (decreasing the effective surface). It is also possible, however, to increase the amplitude or frequency of oscillation and-/or the operating time of the mixer.

Thus, the pestle functions initially in accordance with the invention as an impactor. The powerful oscillation causes the pestle to impact several times against the foil bag transferring all the liquid into the mixing compartment. Transfer is more effective than when, as in known mixing containers, the two parts are only mutually displaced once because the contents of the bag are extensively squeezed out by the multiple impact of the pestle. Since the two parts of the mixing container in accordance with the invention are not mutually displaced to destroy the foil bag accidental and premature destruction is impossible because the bag cannot be destroyed until the pestle is accelerated with great force against it in an oscillating mixer.

The pestle then, once the liquid has been transferred into the mixing chamber, functions as a mixing tool.

To facilitate controlled motion of the pestle, at least the end that faces the foil bag has guides. These guides are preferably radial ribs. Since the pestle therefore slides easily against and is guided to the walls of the mixing chamber without getting stuck. Its impact against the separating foil can be controlled. The pestle accordingly always strikes the same point on the separating foil, and the foil becomes weaker and weaker, finally ripping, at each impact.

The surface of the pestle that faces the separating wall of the foil bag is preferably complementary in shape and size to the inside of the front wall of the second part. If, for example, the inside of the front wall of the second part is concave, the corresponding surface of the pestle is convex. This shortens the time needed to transfer the liquid into the mixing compartment.

When the pestle has radial guide ribs at the head, the apical surfaces of the ribs are the surfaces that impact against the separating foil. The pestle can, however, also be a simple cylinder or a cylinder with a complete head, in which case the surface that impacts against the separating foil is convex if the inside of the front wall of the second part is concave to match.

The mixing container in accordance with the invention preferably has an inside diameter of about 7 to 10 mm, especially about 9 mm, and an overall length of about 30 to 36 mm, especially about 31 mm. Subsequent to assembly, the second, cap-shaped, part can no longer be displaced toward the first part. The second, cap-shaped, part is sleeved over the first part so that the edges of the foil bag come to rest between the two parts, between, that is, the wall of the second part and the first part, so that the bag is securely clamped. This design has several advantages as compared with a design in which the liquid is squeezed out through a rigid perforated wall. The liquid can emerge more easily once the foil bag has opened, for example. The impact of the pestle forces the foil bag flat against the cap-shaped part so that it can be ripped off with it.

The finished mixture of dental preparation cannot become contaminated. The pestle does not force any scraps of foil against the second, cap-shaped part. Although the terminal wall of the first part can be bent, it is preferably straight, in which case the surface of the pestle that faces the terminal wall is also straight so that the pestle moves in a straight line during the mixing process.

The longest diameter of the pestle, which is provided by the ribs in the preferred embodiment of the invention, just allows the pestle to still move freely during the oscillations. Diameters that are 30 to 5%, preferably 15 to 10%, shorter than the inside diameter of the mixing container are preferred. The closer the longest diameter of the pestle approaches the wall of the mixing container, the more satisfactorily it is controlled. The pestle can, however, also be guided by appropriately shaping the second, cap-shaped part.

The length of the pestle also depends on the inside diameter of the mixing container. A length that equals the inside diameter of the mixing container is minimum because if the pestle were any shorter it could not be controlled. The maximum length of the pestle depends on the inside length of the mixing container. The maximum length of the pestle is approximately 10 to 60%, preferably 20 to 40%, of the inside length of the mixing container. In one preferred embodiment of the invention in which the guides are radial ribs, they are located on the head of the pestle that faces the foil bag. Two or three ribs are generally sufficient, although the control of the pestle is improved by four ribs or more. Guides in the form of points or other shapes are also possible.

The elevation on the front of the pestle is preferably a spike, cone, or point. It facilitates opening the foil bag. The length of this elevation depends on the thickness of the filled bag, which should not be exceeded. The minimum length of the elevation should at least equal the thickness of the separating foil. The length of the elevation is generally 0.5 to 3 mm, preferably 1 to 2 mm.

The pestle can in principle be made out of metal, glass, or plastic. A plastic with an impact strength that is high enough to resist the oscillations of the mixer is preferred.

The liquid is contained directly in a foil bag in the cap-shaped second part. Such a bag can be made in accordance with the invention of foil or plastic film, foil, especially aluminum foil, preferably coated with a thermoplastic. The separating walls of the foil bag are heat-sealed together at their edges. The preferred bags are completely moisture-tight such that no oxidation occurs when the liquid is mercury, for example, even over the long term.

In addition to the manufacture of amalgams, the mixing container in accordance with the invention can also be employed to store and mix materials for manufacturing other dental preparations such as dental cements—phosphate, silicate, and carboxylate cements, for example.

BRIEF DESCRIPTION OF DRAWINGS

One embodiment of the invention will now be specified by way of example with reference to the drawings, in which.

DESCRIPTION OF SPECIFIC EMBODIMENT

Figure 1:
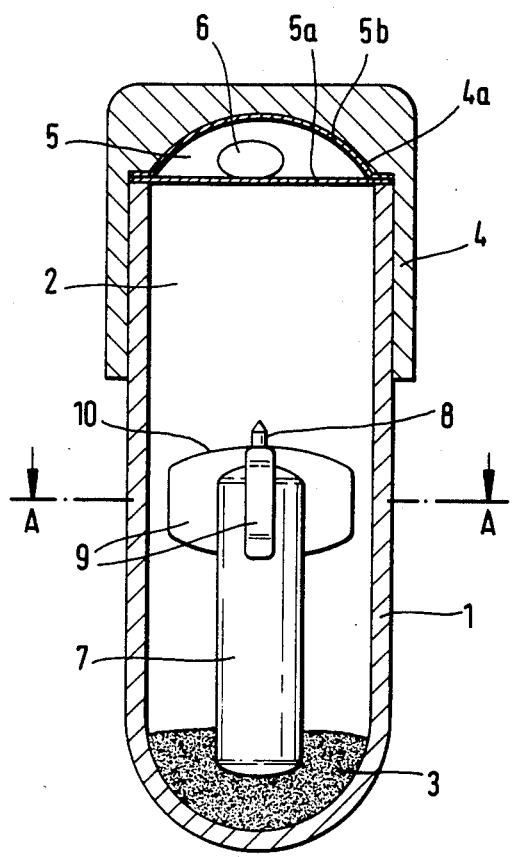
FIG. 1 is a longitudinal section through a mixing container in accordance with the invention and FIG. 2 is a section along the line A—A in FIG. 1.
Figure 2:
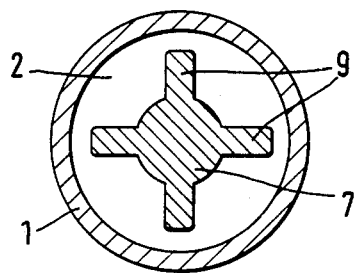

The mixing container in accordance with the invention has a part 1 in the nature of a housing that defines a mixing compartment 2. Compartment 2 contains a normally powdered, material 3 (silver powder for example). The first part 1 is closed off by a second, separable, cap-shaped part 4 with a vaulted inside front wall 4a. A bag 5 of thermoplastic-covered aluminum foil is inserted in part 4. A liquid 6 (mercury for example) is sealed into bag 5. Bag 5 is defined by separating foils 5a and 5b that are heat-sealed together liquid-tight at the edges by a known process. The edges are clamped tight between the first and second parts of the container Foil 5b is beveled against the inside of the front wall 4a of second part 4.

Foil 5a is a destructible separating foil. It can be provided with pre-set ripping points (not illustrated). It faces a pestle 7. Pestle 7 is generally cylindrical. The end of pestle 7 that faces separating foil 5a has a point 8 that can penetrate separating foil 5a when the mixing container is intensively shaken in an oscillating mixer. The end of pestle 7 that faces separating foil 5a also has radial guide ribs 9 to control the motion of the pestle and prevent it from skewing during the mixing process. The front of pestle 7 is vaulted at the top 10 of the ribs to match the vaulting of front wall 4a of second part 4 so that the apical surfaces of ribs 9 force separating foil 5a against separating foil 5b when the pestle impacts against bag 5, leaving practically no space between the foils.

Upon completion of the mixing process, which lasts only a few seconds, second part 4 is removed with the flattened bag, following which pestle 7 and then the prepared amalgam are removed from mixing compartment 2.

What is claimed is:

1. A mixing container for separately storing and mixing interactive materials used in manufacturing dental preparations, comprising a first part in the form of a mixing compartment (2) which contains a normally powdered material; and a second separable cup shaped part (4) separated by a separating wall from the mixing compartment and containing a liquid, the mixing compartment comprising a movable oblong pestle, said separating wall being a wall facing said mixing compartment (2), and defining a liquid-filled destructible foil bag (5) in said second part (4), the tear strength of said separating wall and the pressure impulse imparted by the pestle (7) when the container is shaken in an oscillating mixer are matched so as to result in the destruction of the said foil bag when struck by the pestle, wherein at least the end of the pestle (7) which faces the foil bag (5) has guides (9), and wherein the end (10) of the pestle (7) that faces the separating wall (5a) is complementary in shape and size to the inside of the front wall (4a) of the second part (4).

2. A mixing container according to claim 1, wherein the separating wall (5a) of the foil bag (5) that faces the mixing compartment (2) has a pre-set ripping point in the central area of said separating wall.

3. A mixing container according to claim 1, wherein the end of the pestle (7) that faces the foil bag (5) has an elevation (8) to increase the pressure impulse.

4. A mixing container according to claim 3, wherein the elevation (8) is a point.

5. A mixing container according to claim 1, wherein the guides (9) are radial ribs.

6. A mixing container according to claim 1, wherein the end (10) has a convex shape and said front wall is concave.

7. A mixing container according to claim 1, wherein the end (10) has a concave shape and said front wall is convex.

8. A mixing container according to claim 1 wherein said foil bag (5) has edges which are clamped between the first (1) and the second (4), parts.

9. A mixing container according to claim 1 wherein said second part is cap-shaped.

10. A mixing container according to claim 8 wherein said second part is cap-shaped.

11. A mixing chamber according to claim 1, wherein said powder is silver.

12. A mixing chamber according to claim 1, wherein said liquid is mercury.

13. A mixing chamber according to claim 12 wherein said liquid is mercury.

* * * * *